United States Patent
Gaynor et al.

(10) Patent No.: US 9,296,680 B2
(45) Date of Patent: Mar. 29, 2016

(54) METHOD OF MAKING AMORPHOUS RESIN FOR USE IN ROBUST SOLID INK APPLICATIONS

(75) Inventors: Roger E. Gaynor, Oakville (CA); Tila Tahmoures-Zadeh, Thornhill (CA)

(73) Assignee: XEROX CORPORATION, Norwalk, CT (US)

( * ) Notice: Subject to any disclaimer, the term of this patent is extended or adjusted under 35 U.S.C. 154(b) by 1156 days.

(21) Appl. No.: 13/306,549

(22) Filed: Nov. 29, 2011

(65) Prior Publication Data

US 2013/0137891 A1 May 30, 2013

(51) Int. Cl.
*C07C 67/08* (2006.01)

(52) U.S. Cl.
CPC ............. *C07C 67/08* (2013.01); *C07C 2101/14* (2013.01)

(58) Field of Classification Search
None
See application file for complete search history.

(56) References Cited

U.S. PATENT DOCUMENTS

| | | | |
|---|---|---|---|
| 5,372,852 A | 12/1994 | Titterington et al. | |
| 6,547,380 B2 | 4/2003 | Smith et al. | |
| 8,308,859 B1 * | 11/2012 | Belelie | C09D 11/38 106/31.29 |
| 9,051,486 B2 * | 6/2015 | Belelie | C09D 11/34 |
| 2012/0272860 A1 * | 11/2012 | Belelie | C09D 11/38 106/31.13 |
| 2012/0277462 A1 * | 11/2012 | Enright et al. | 560/180 |
| 2012/0291663 A1 * | 11/2012 | Belelie | C09D 11/38 106/31.13 |
| 2014/0041546 A1 * | 2/2014 | Belelie | C09D 11/34 106/31.13 |

OTHER PUBLICATIONS

Buschhaus et al., Synthesis and chiroptical properties of a new type of chiral depsipeptide dendrons. Tetrahedron, 2003, 59, 3899-3915.*

* cited by examiner

*Primary Examiner* — Michael Barker
*Assistant Examiner* — Po-Chih Chen
(74) *Attorney, Agent, or Firm* — Pillsbury Winthrop Shaw Pittman LLP

(57) ABSTRACT

Methods for making amorphous resins for use in robust solid ink applications are disclosed in which an organic acid is reacted with an alcohol in the presence of a solvent in the amount of from about 0.5 to about 1.5 grams of solvent per gram of reaction product. The reaction product is an ester of tartaric acid or an ester of citric acid.

16 Claims, No Drawings

METHOD OF MAKING AMORPHOUS RESIN FOR USE IN ROBUST SOLID INK APPLICATIONS

BACKGROUND

Ink jetting devices are known in the art, and thus extensive description of such devices is not required herein. As described in U.S. Pat. No. 6,547,380, which is hereby incorporated by reference herein in its entirety, ink jet printing systems generally are of two types: continuous stream and drop-on-demand. In continuous stream ink jet systems, ink is emitted in a continuous stream under pressure through at least one orifice or nozzle. The stream is perturbed, causing it to break up into droplets at a fixed distance from the orifice. At the break-up point, the droplets are charged in accordance with digital data signals and passed through an electrostatic field that adjusts the trajectory of each droplet in order to direct it to a gutter for recirculation or a specific location on a recording medium. In drop-on-demand systems, a droplet is expelled from an orifice directly to a position on a recording medium in accordance with digital data signals. A droplet is not formed or expelled unless it is to be placed on the recording medium.

There are at least three types of drop-on-demand ink jet systems. One type of drop-on-demand system is a piezoelectric device that has as its major components an ink filled channel or passageway having a nozzle on one end and a piezoelectric transducer near the other end to produce pressure pulses. Another type of drop-on-demand system is known as acoustic ink printing wherein an acoustic beam exerts a radiation pressure against objects upon which it impinges. Still another type of drop-on-demand system is known as thermal ink jet, or bubble jet, and produces high velocity droplets.

In a typical design of a piezoelectric ink jet device utilizing phase change or solid inks printing directly on a substrate or on an intermediate transfer member, such as the one described in U.S. Pat. No. 5,372,852, which is hereby incorporated by reference herein in its entirety, the image is applied by jetting appropriately colored inks during four to eighteen rotations (incremental movements) of a substrate (an image receiving member or intermediate transfer member) with respect to the ink jetting head, i.e., there is a small translation of the print head with respect to the substrate in between each rotation. This approach simplifies the print head design, and the small movements ensure good droplet registration. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops.

As noted, ink jet printing processes may employ inks that are solid at room temperature and liquid at elevated temperatures. Such inks may be referred to as hot melt inks or phase change inks. Advantages of a phase change ink in ink jet printing are elimination of potential spillage of the ink during handling, a wide range of print density and quality, minimal paper cockle or distortion, and enablement of indefinite periods of nonprinting without the danger of nozzle clogging, even without capping the nozzles.

Solid inks for piezoelectric ink jet printing have been designed to successfully print in a transfix mode wherein the ink is jetted onto an intermediate transfer drum. In the transfix printing process, the ink cools from the jetting temperature (broadly, from about 75° C. and to no higher than about 180° C., and typically from about 110° C. to about 140° C.) to the drum temperature (typically from about 50° C. to about 60° C.), and, subsequently, as a substantially solid phase, the ink is pressed into a paper substrate. Such a process provides a number of advantages including vivid images, economy of jet use, and substrate latitude among porous papers. However, such ink designs can present problems when applied to coated papers. In general, the ink and the print process can fail to provide sufficient image durability in response to paper handling stresses such as scratch, fold and rub stresses.

A need remains for amorphous materials to provide certain characteristics to the printed ink, such as tack and robustness. Current processes for preparing amorphous material require use of a large amount of solvent and long reaction times, sometimes in excess of 45 hours. Current solvent-less reaction process for making amorphous resins for use in robust solid ink applications sometimes take in excess of 20 hours to complete. Moreover, while the reaction itself may not require a solvent, or very little solvent, significant amounts of solvent typically are used in the isolation and purification of the resulting amorphous resin component. As a consequence, a need remains for an improved process for preparing phase change or solid ink components that is cost effective, environmentally friendly, and efficient.

SUMMARY

According to embodiments illustrated herein, there is provided a method of making an amorphous resin by reacting at least one organic acid of the formula R'COOH with at least one alcohol of the formula R—OH, in the presence of a solvent in an amount of from about 0.5 to about 1.5 grams of solvent per gram of product to form a reaction product selected from: (a) an ester of tartaric acid of the formula:

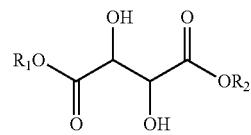

wherein the tartaric acid backbone is selected from the group consisting of L-(+)-tartaric acid, D-(−)-tartaric acid, DL-tartaric acid, mesotartaric acid, and mixtures thereof; or (b) an ester of citric acid of the formula:

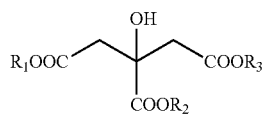

wherein R', R, $R_1$, $R_2$, and $R_3$ can be the same or different, and wherein R', R, $R_1$, $R_2$, and $R_3$ are each independently selected from: (i) an alkyl group, which may be linear or branched, saturated or unsaturated, cyclic or acyclic, substituted or unsubstituted, and wherein heteroatoms either may or may not be present in the alkyl group; (ii) an aryl group, which may be substituted or unsubstituted, and wherein heteroatoms either may or may not be present in the aryl group; (iii) an arylalkyl group, which may be substituted or unsubstituted, wherein the alkyl portion of the arylalkyl group can be linear or branched, saturated or unsaturated, cyclic or acyclic, substituted or unsubstituted, and wherein heteroatoms either may or may not be present in either the aryl or the alkyl portion of the arylalkyl group; or (iv) an alkylaryl group, which may be substituted or unsubstituted, wherein the alkyl portion of the alkylaryl group can be linear or branched, saturated or unsaturated, cyclic or acyclic, substituted or unsubstituted, and wherein heteroatoms either may or may not be present in either the aryl or the alkyl portion of the alkylaryl group

DETAILED DESCRIPTION

In the following description, it is understood that other embodiments may be utilized and structural and operational changes may be made without departure from the scope of the present embodiments disclosed herein.

The process herein presents an improvement over solvent-based and solvent-less reactions for making amorphous resins for use in robust solid ink applications. The solvent-based reaction mechanism utilizes significant amounts of solvent (e.g., on the order of 5-15 grams of solvent per gram of product) and takes an extended period of time to provide an appreciable yield of product. The solvent-less reaction mechanism, while not involving solvent in the reaction, still requires a significant amount of solvent to isolate, separate, and/or purify the product. In addition, the solvent-less reaction process also takes an extended period of time to provide an appreciable yield of product.

The present inventors have discovered that the addition of a small amount of solvent, e.g., on the order of from about 0.5 to about 1.5 grams of solvent per gram of product, during the reaction, provides an improved yield, and overall reduction of total solvent required. The use of a small amount of solvent during the reaction can reduce the amount of time to produce an appreciable yield of product (from about 65% to 80%) to anywhere from about 1 hour to less than 10 hours. These results are surprising and unexpected when compared to the known solvent-based and solvent-less reaction schemes.

In accordance with the embodiment, there is provided a method of making an amorphous resin by reacting at least one organic acid of the formula R'COOH with at least one alcohol of the formula R—OH, in the presence of a solvent in an amount of from about 0.5 to about 1.5 grams of solvent per gram of product and optionally in the presence of a catalyst to form a reaction product; optionally, heating the reaction mixture; and optionally isolating the reaction product; wherein the reaction product is either: (a) an ester of tartaric acid of the formula:

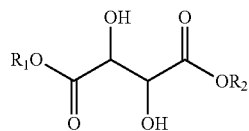

wherein the tartaric acid backbone is selected from L-(+)-tartaric acid, D-(−)-tartaric acid, DL-tartaric acid, mesotartaric acid, and mixtures thereof; or (b) an ester of citric acid of the formula:

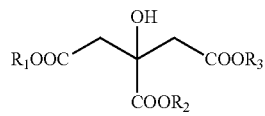

Wherein R', R, $R_1$, $R_2$, and $R_3$ can be the same or different, and wherein R', R, $R_1$, $R_2$, and $R_3$ are each independently selected from: (i) an alkyl group, having from about 1 to about 40, or from about 1 to about 20, or from about 1 to about 10 carbon atoms, which may be linear or branched, saturated or unsaturated, cyclic or acyclic, substituted or unsubstituted, and wherein heteroatoms either may or may not be present in the alkyl; (ii) an aryl group, having from about 3 to about 40, or from about 6 to about 20, or from about 6 to about 10 carbon atoms, which may substituted or unsubstituted, and wherein heteroatoms either may or may not be present in the aryl; (iii) an arylalkyl group, having from about 4 to about 40, or from about 7 to about 20, or from about 7 to about 12 carbon atoms, although the number of carbon atoms can be outside of these ranges, which may be substituted or unsubstituted, wherein the alkyl portion of the arylalkyl group can be linear or branched, saturated or unsaturated, cyclic or acyclic, substituted or unsubstituted, and wherein heteroatoms either may or may not be present in either the aryl or the alkyl portion of the arylalkyl group; or (iv) an alkylaryl group, having from about 4 to about 40, or from about 7 to about 20, or from about 7 to about 12 carbon atoms, although the number of carbon atoms can be outside of these ranges, which may be substituted or unsubstituted, wherein the alkyl portion of the alkylaryl group can be linear or branched, saturated or unsaturated, cyclic or acyclic, substituted or unsubstituted, and wherein heteroatoms either may or may not be present in either the aryl or the alkyl portion of the alkylaryl group.

The organic acid (R'COOH) used for the process herein can be any suitable or desired organic acid. In embodiments, at least one organic acid comprising one, two, or three carboxylic acid groups is employed. In certain embodiments, the at least one organic acid is selected from the group consisting of acetic acid, propanoic acid, butanoic acid, pentanoic acid, citric acid, hexanoic acid, heptanoic acid, octanoic acid, decanoic acid, dodecanoic acid, tridecanoic acid, lauric acid, stearic acid, tartaric acid, and mixtures and combinations thereof. In an embodiment, the at least one organic acid is tartaric acid. In another embodiment, the at least one organic acid is citric acid.

The alcohol used in the reaction (R—OH) can be any suitable alcohol for carrying out the reaction. In embodiments, the alcohol can be one or more R—OH compounds, such as a compound of the formula $R_1$—OH, $R_2$—OH, $R_3$—OH, or a mixture thereof, wherein $R_1$, $R_2$, and $R_3$ are the same or different, and wherein $R_1$, $R_2$, and $R_3$ are each independently selected from the definitions for R in ROH as described above, and wherein, in embodiments, $R_1$, $R_2$, and $R_3$ are each independently selected from an alkyl group having from about 1 to about 40 carbon atoms; an aryl group having from about 3 to about 40 carbon atoms; an alkylaryl group having from about 4 to about 40 carbon atoms; and an arylalkyl group having from about 4 to about 40 carbon atoms.

In certain embodiments, R—OH is selected from the group consisting of

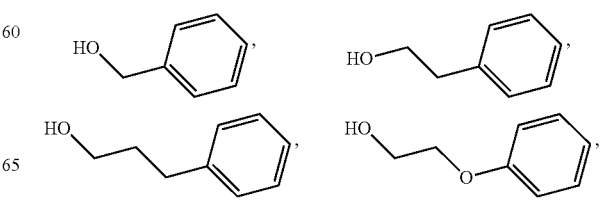

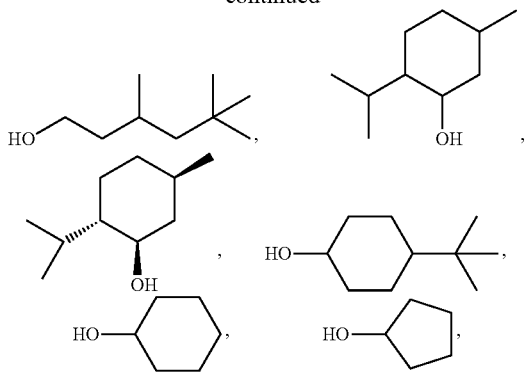

and mixtures thereof.

The organic acid (R'COOH) and the alcohol (ROH) can be provided in any desired or effective amounts. In one embodiment, the carboxylic acid and alcohol are provided in a ratio of organic acid to alcohol within the range of from about 1:1 to about 1:3, or from about 1:1 to about 1:2, or from about 1:15 to about 1.18.

The solvent used in the reaction can be any solvent suitable for carrying out the reaction between the organic acid and alcohol. In embodiments, the solvent can be particularly suitable for use at the reaction temperatures described herein. Examples of suitable solvents include one or more selected from the group consisting of pentane, hexane, cyclohexane, heptane, octane, nonane, decane, undecane, dodecane, tridecane, tetradecane, toluene, xylene, benzene, mesitylene, and mixtures thereof. In an embodiment, the solvent is mesitylene. The amount of solvent is within the range of from about 0.5 to about 1.5 grams of solvent per gram of product, or from about 0.65 to less than 1 grams of solvent per gram of product, or from about 0.75 to about 0.85 grams of solvent per gram of product.

The present process can be carried out at any suitable or desired temperature. In embodiments, heating the reaction mixture comprises heating to a temperature of from about 40 to about 250° C., or from about 90 to about 200° C., or from about 130 to about 180° C., although not limited to these ranges. In an embodiment, the reaction can be carried out at a temperature of about 155 to about 160° C. In embodiments, the reaction temperature profile can be selected to increase the reaction rate.

The reaction can be heated for any suitable or desired amount of time. In embodiments, heating the reaction mixture comprises heating for a period of from about 1 to about 10 hours, or from about 2 to about 8 hours, or from about 3 to about 6 hours.

In an embodiment, heating the reaction mixture comprises heating to a temperature of from about 40 to about 250° C. for a period of from about 1 to about 10 hours. In another embodiment, heating the reaction mixture comprises heating to a temperature of from about 130 to about 180° C. for a period of from about 2 to about 8 hours. In yet another embodiment, heating the reaction mixture comprises heating to a temperature of 155-160° C. for a period of about 3 to about 6 hours, or about 5 hours with azeotropic removal of water. Heating to the reaction temperature allows the azeotropic removal of water from the reaction, and the dissolution of the product.

Any suitable or desired catalyst can be used for the present reaction process. Examples of suitable catalysts include, but are not limited to, those selected from the group consisting of sulfuric acid, phosphoric acid, hydrochloric acid, p-toluene-sulfonic acid (PTSA), zinc chloride, magnesium chloride, zinc acetate, magnesium acetate, dibutyl tin laurate, and butylstannoic acid, and mixtures and combinations thereof. In one embodiment, the catalyst may be selected from the Fascat® series of catalysts available from Arkema, Inc., such as Fascat® 4100. The catalyst can be selected in any effective amount. For example, the catalyst can be present in an amount of from about 0.01 to about 1 percent by weight of the reaction mixture, or from about 0.1 to about 0.5 percent by weight of the reaction mixture. In an embodiment, PTSA is used as the catalyst in an amount of about 0.2 percent by weight of the reaction mixture.

The process may include additional process steps. The process can further comprise steps of cooling and isolating the product which steps can be performed according to the knowledge of a person having ordinary skill in the art. Various techniques for these processing steps are known in the chemical arts.

In embodiments, the process comprises cooling the reaction mixture to a temperature from about room temperature to about 100° C., and carrying out a series of aqueous extraction washes followed by phase separations. For example, the reactor contents may be cooled to a temperature of from about 65 to about 95° C., or about 80° C., treated with deionized water at 80° C., agitated for about 5 to about 20 minutes, or about 5 minutes, and then allowed to stand without stirring to allow for phase separation. Phase separation then can be carried out by allowing the product to settle for a period of from about 15 minutes to about 1 hour, or from about 25 minutes to about 40 minutes, and then separating the aqueous phase using techniques known in the art (e.g., drawing the aqueous phase from the reaction vessel by use of a valve discharge).

The organic/product phase may then be treated with one or more hot acetic acid solutions (e.g., using two washes, 6 wt % and 2 wt % acetic acid) wherein the mixture is initially agitated for about 5 to about 20 minutes, or for about 5 minutes, and then allowed to stand without stirring to allow for phase separation. Aqueous phase separation can be carried out between each sodium hydroxide extraction, as described above.

The organic/product phase then may be treated one or more times with a hot sodium hydroxide solution (or a 2% aqueous solution), wherein the mixture is initially agitated for about 5 to about 20 minutes, or for about 5 minutes, and then allowed to stand without stirring to allow for phase separation. Aqueous phase separation can be carried out between each sodium hydroxide extraction, as described above. A final hot deionized water extraction can be carried out, followed by phase separation, as described above, to prepare the final product.

The final purification can be removal of water and/or solvent, such as through evaporation or distillation. For example, solvent may be removed by use of vacuum with an inert gas sweep to aide in the removal. When solvent removal is complete, the final product can be discharged hot (e.g., from about 65 to about 95°, or about 80° C.) and subsequently cooled to produce the amorphous resin product. The process may further include any additional chemical synthesis steps according to the knowledge of a person having ordinary skill in the art.

In one embodiment, the reaction product herein can be a compound selected from: (a) an ester of tartaric acid of the formula:

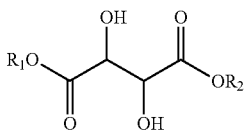

wherein the tartaric acid backbone is selected from L-(+)-tartaric acid, D-(−)-tartaric acid, DL-tartaric acid, mesotartaric acid, and mixtures thereof; or (b) an ester of citric acid of the formula:

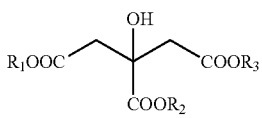

wherein R', R, $R_1$, $R_2$, and $R_3$ are defined as above.

In an embodiment, the reaction product is a compound having the formula:

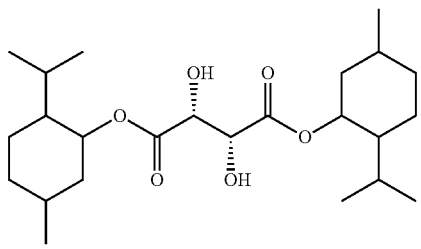 [SMILES: CC1CCC(C(C)C)C(OC(=O)[C@H](O)[C@@H](O)C(=O)OC2CC(C)CCC2C(C)C)C1]

In certain embodiments, the methods described herein are capable of producing the amorphous resin (e.g., ester of tartaric acid or citric acid) in a yield of from about 50% to about 90%, or from about 65% to about 85%, or from about 70% to about 80% in less than 10 hours, or from about 3 to about 6 hours of reaction time. The amorphous resin product can have a viscosity within the range of from about 5 to about 15 cps at 140°, or from about 7 to about 11 cps, and a glass transition temperature within the range of from about 10 to about 20° C., or from about 15 to about 17° C. In further embodiment, the reaction throughput is about 420 grams of product per liter of reactor space.

EXAMPLES

The example set forth herein below is illustrative of different compositions and conditions that can be used in practicing the present embodiments. All proportions are by weight unless otherwise indicated. It will be apparent, however, that the embodiments can be practiced with many types of compositions and can have many different uses in accordance with the disclosure above and as pointed out hereinafter.

Comparative Example

This example describes a method of making an ester of tartaric acid using a solvent-less reaction method, followed by isolation, purification and extraction of the product, which includes the use of a solvent. The solvent-less reaction to produce Di-DL-mentholester of L-tartaric acid proceeds in accordance with the reaction sequence provided below:

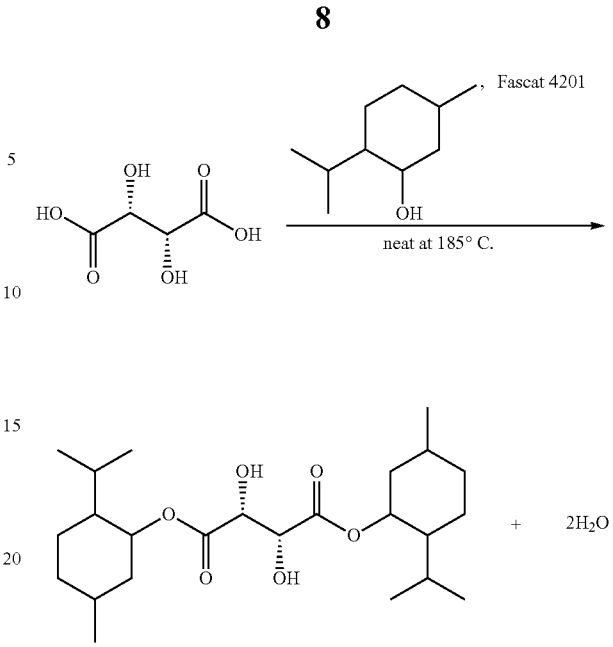

The method of making the Di-DL-mentholester of L-tartaric acid was carried out as follows. In a 100 ml flask, equipped with a Dean-Stark trap, L-tartaric acid (10 g, 66.6 mmol), DL-menthol (20.82 g, 133 mmol), and Fascat 4201 catalyst (0.030 g, 0.12 mmol) were added. The mixture was heated using a heating mantle to 185° in 30 minutes. Heating was continued overnight. After 19 hours, no water was collected in the Dean-Stark trap (theoretical 2.39 ml). The pressure was reduced slowly to ~1 mmHg (using a vacuum pump) to facilitate water removal. ~1.0 ml total water was removed after about 10 minutes. The reaction mixture was cooled down to 120° C. under argon and pour into an aluminum dish to cool down.

The crude product was removed from the dish and re-dissolved in 200 ml toluene (heated to dissolve) and was washed with aqueous solution of 10 wt % KOH, three brine washes, and dried with $Mg_2SO_4$ followed by filtration to remove the solid waste. The organic solution containing the product was concentrated using a rotovap, then the solution was placed in a vacuum oven at 120° C. for final solvent removal and drying, yielding 12.92 g (45.5%) product.

This process has a number of practical drawbacks, including one or more of the following: (a) the long reaction times and low isolated product yields; (b) the large volume of solvent required for the purification step and difficulty in removing reaction by-products; (c) the reaction rate is reduced because the reaction is limited by the slow rate of water removal from the system; and (d) the product isolation step requires the removal of a large amount of solvent by a rotovap and vacuum oven drying, making for a difficult product isolation which is not practical at a full manufacturing scale.

Inventive Example 1

The example provides a method of making an ester of tartaric acid using the inventive method in which a small amount of solvent were used during the reaction, followed by extraction of the product. The inventive method of making a Di-DL-mentholester of L-tartaric acid proceeds in accordance with the reaction sequence provided below:

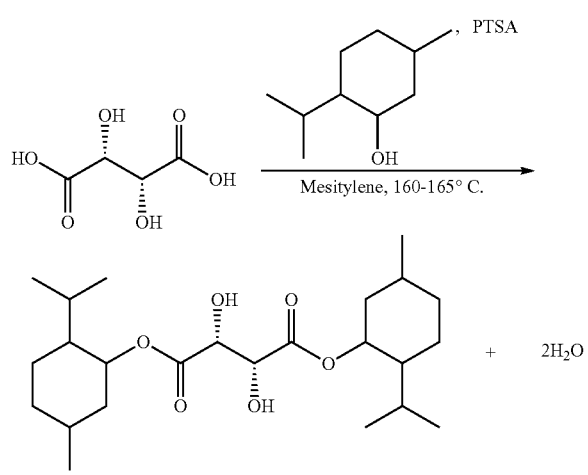

The method of making the Di-DL-mentholester of L-tartaric acid was carried out as follows. This method proposes the use of a solvent suitable for the required temperature range of the process and a catalyst more compatible for the reaction and solvent system, than that used in the comparative example above. This embodiment uses mesitylene, with a boiling point of 164.7° C. for azeotropic removal of the water of reaction and for the dissolution of the tartaric acid at the reaction temperature of 150-160° C.

In a 1 L jacketed-glass reactor equipped with a Dean-Stark trap, L-tartaric acid (228.1 g, 1.52 mol), DL-menthol (428.2 g, 2.74 mol), and mesitylene (344 g) were added to give a suspension. p-Toluenesulfonic acid monohydrate (3.5 g, 0.018 mol) was added and the mixture was heated to 155-160° C. for 5 hours with azeotropic removal of water. Reaction conversion was monitored by the volume of water that was removed through the Dean-Stark trap, and samples were taken for HPLC reaction monitoring. The reactor contents were cooled to 80° C.

A series of aqueous extraction washes followed by phase separations were carried out. About 500 g Hot (80° C.) deionized water was added slowly, the reactor contents were stirred for 5 minutes and then agitation stopped to allow for phase separation. After 30 minutes settling, the aqueous phase was separated at the reactor bottom valve discharge. A hot 2 wt % NaOH aqueous solution was added and stirred for 5 minutes, followed by settling for 30 minutes prior to separation of the aqueous phase. A second hot 2 wt % NaOH aqueous extraction was carried out. This was followed by a final 500 g Hot deionized extraction and phase separation.

In one embodiment, the extraction washing procedure uses one hot deionized water wash, followed by two hot acetic acid washes (6 wt %, then 2 wt %), followed by three hot NaOH washes (2 wt %, 2 wt %, and 1 wt %). The hot deionized water washes followed by phase separations were carried out until the aqueous waste washes were at pH 6.5-7 and have a conductivity of less than 100 μS/cm.

The final solvent (mesitylene) removal was carried out under vacuum with a nitrogen sweep to aide removal. The agitator rpm was increased and the reactor jacket set to 100° C. to effect the controlled removal of the mesitylene. When no more solvent was coming off, the product was discharged hot (greater than 80-85° C.) to metal tray. Approximately 420 g of the amorphous resin product was recovered (typical yield ~70-80%).

Inventive Example 2

Inventive example 1 was repeated as stated above. The reproduction of inventive example 1 yielded about 393 grams of product with a slightly lower viscosity.

A comparison between the products produced according to the comparative example, and products produced according to Inventive Examples 1 and 2 are shown in Tables 1 and 2 below.

TABLE 1

| Sample ID | T g (° C.) | Yield (g) | Yield (%) | Acid # | Viscosity (n@140° C.) (cps) |
|---|---|---|---|---|---|
| Comparative | 14.94 | 12.92 | 45.5% | 2.81 | 8.61 |
| Example 1 | 16.88 | 420 | 77.9 | 3.48 | 10.35 |
| Example 2 | 16.08 | 393 | 73.41 | 1.68 | 7.45 |

TABLE 2

| process | g solvent/g product |
|---|---|
| Comparative | 13.4 |
| Inventive | 0.82 |

The above tables reveal that use of a small amount of solvent during the reaction, for example, a solvent compatible with the reaction processing conditions, results in a dramatically improved yield in product in a far shorter period of time. The tables also show that the use of a small amount of suitable solvent during the reaction eliminates the need for excess solvent used in the isolation, purification, and extraction of the amorphous resin, resulting in a reduction of overall solvent by orders of magnitude. The examples reveal that an amorphous resin product can be produced in over 30% greater yield, in about ¼ of the amount of time, using about 16 times less solvent.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:
1. A method of making an amorphous resin, comprising the steps of:
reacting a tartaric acid with at least one alcohol of the formula R—OH, for a period of time, and at a temperature, in the presence of an optional catalyst, and a solvent in an amount of from 0.65 to less than 1 grams of solvent per gram of an ester of tartaric acid of the formula:

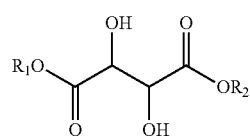

wherein the at least one alcohol of the formula R—OH is selected from the group consisting of

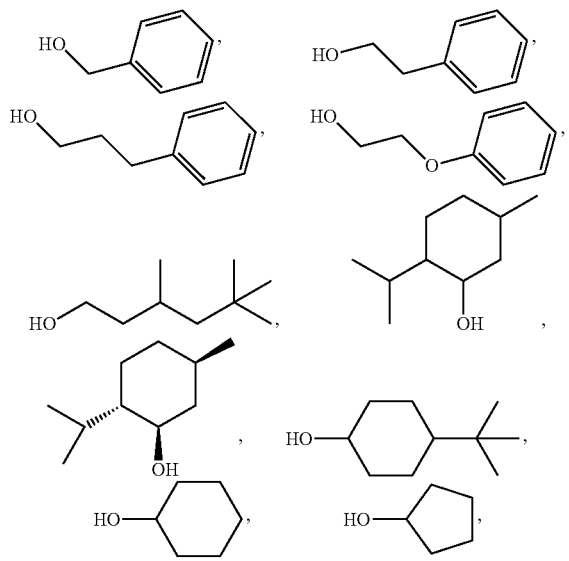

and mixtures thereof
wherein $R_1$ and $R_2$ are each independently selected from the definitions for R in ROH;
wherein the tartaric acid is selected from the group consisting of L-(+)-tartaric acid, D-(−)-tartaric acid, DL-tartaric acid, mesotartaric acid, and mixtures thereof.

2. The method of claim 1, wherein the alcohol is

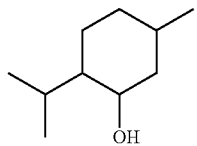

3. The method of claim 1, wherein the solvent is one or more solvents selected from the group consisting of pentane, hexane, cyclohexane, heptane, octane, nonane, decane, undecane, dodecane, tridecane, tetradecane, toluene, xylene, benzene, mesitylene, and mixtures thereof.

4. The method of claim 3, wherein the solvent is mesitylene.

5. The method of claim 1, wherein the amount of solvent used is from about 0.75 to about 0.85 grams of solvent per gram of product.

6. The method of claim 1, wherein the reaction is carried out in the presence of a catalyst selected from the group consisting of sulfuric acid, phosphoric acid, hydrochloric acid, p-toluenesulfonic acid (PTSA), zinc chloride, magnesium chloride, zinc acetate, magnesium acetate, dibutyl tin laurate, and butylstannoic acid, and mixtures and combinations thereof.

7. The method of claim 6, wherein the catalyst is PTSA.

8. The method of claim 1, wherein the reacting step is performed at a temperature from about 40 to about 250° C.

9. The method of claim 8, wherein the temperature is from about 155 to about 160° C.

10. The method of claim 1, wherein the reacting step is carried out for a period of time from about 1 to about 10 hours.

11. The method of claim 10, wherein the reacting step is carried out for a period of time from about 3 to about 6 hours.

12. The method of claim 8, further comprising cooling the reaction to a temperature from about 65° C. to about 95° C.

13. The method of claim 1, further comprising subjecting the ester of tartaric acid to aqueous extraction and phase separation.

14. The method of claim 1, wherein the ester of tartaric acid is a compound of the formula:

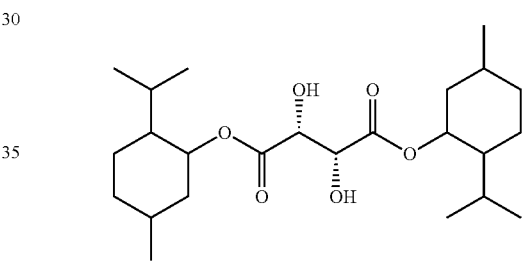

15. The method of claim 1, wherein the reacting step produces the ester of tartaric acid in a yield of from about 70% to about 80% in less than 10 hours.

16. The method of claim 1, wherein the method affords a reaction throughput to be about 420 grams of product per liter of reactor space.

* * * * *